United States Patent [19]
Fordham et al.

[11] Patent Number: 6,115,671
[45] Date of Patent: Sep. 5, 2000

[54] METHOD FOR ESTIMATING ROCK PETROPHYSICAL PARAMETERS USING TEMPERATURE MODIFIED NMR DATA

[75] Inventors: Edmund J. Fordham, Danbury; Mark Flaum, Ridgefield; Terizhandur S. Ramakrishnan, Bethel; William E. Kenyon, Ridgefield; David Allen, Brookfield, all of Conn.

[73] Assignee: Schlumberger Technology Corporation, Ridgefield, Conn.

[21] Appl. No.: 09/243,563

[22] Filed: Feb. 3, 1999

[51] Int. Cl.$^7$ .................................................. G06F 19/00
[52] U.S. Cl. .................................................. 702/8; 324/303
[58] Field of Search .................................... 702/8; 324/303

[56] References Cited

U.S. PATENT DOCUMENTS

| | | | |
|---|---|---|---|
| 4,710,713 | 12/1987 | Strikman | 324/303 |
| 5,055,787 | 10/1991 | Kleinberg et al. | 324/303 |
| 5,289,124 | 2/1994 | Jerosch-Herold et al. | 324/303 |
| 5,680,043 | 10/1997 | Hurlimann et al. | 324/303 |

*Primary Examiner*—Donald McElheny, Jr.
*Attorney, Agent, or Firm*—William B. Batzer; Salzman & Levy

[57] ABSTRACT

Carbonate formations yield unreliable, down hole NMR results. Inter alia, these results must be corrected for temperature. The invention features several methods for obtaining more reliable NMR results for rock petrophysical parameters in carbonate rock formations based upon adjusting $T_2$ data with respect to temperature.

22 Claims, 7 Drawing Sheets

METHOD FOR ESTIMATING ROCK PETROPHYSICAL PARAMETERS USING TEMPERATURE MODIFIED NMR DATA

FIELD OF THE INVENTION

The invention relates to a method for estimating rock petrophysical parameters of underground rock formations in oil and gas wells and, more particularly, to a process for utilizing temperature modified NMR data that yields more accurate petrophysical interpretations in carbonate rocks.

BACKGROUND OF THE INVENTION

Nuclear Magnetic Resonance (NMR) as a well logging technique does not always yield useful results. Part of the problem with NMR logging is a consequence of faulty assumptions, particularly as they apply to carbonate rocks. Carbonates are particularly troublesome because great variations in their pore sizes and organic materials distributed throughout the grains can cause misleading results. Conventional interpretation of NMR measurements is based on a number of potentially faulty assumptions, to wit:

1) In addition to the bulk relaxation mechanism, magnetization decays because water molecules diffuse to the surface of the grain where they experience an enhanced relaxation rate. This is assumed to be a result of their interaction with local magnetic fields associated with paramagnetic impurities in the grain.

2) The pore space is divided into separate pores that do not interact with each other.

3) Within each pore, magnetization is assumed to be uniform. The basis for the latter assumption is that $\rho V_s/D \ll 1$, where D is the diffusion coefficient in the bulk fluid, $V_s$ is the volume to surface ratio of the pore, and $\rho$ is the surface relaxivity. The characteristic decay time constant of spin-spin relaxation of any pore is then given as:

$$1/T_2 = \rho/V_s + 1/T_{2b} \quad (1)$$

where $T_{2b}$ is the bulk relaxation time.

4) The magnetization decay can be represented as an integral of contributions of all such components due to the multitude of pores of different volume to surface ratio. If the probability density function of $T_2$ is $g(T_2)$, this integral can then be resolved into the components represented by $g(T_2)$ by a number of established fitting procedures. In practice, $g(T_2)$ is widely considered to represent the pore size distribution.

The above assumptions are flawed in general, and particularly several of them do not hold for carbonate rocks. The measured decay is not readily translatable to pore sizes. (Assumption 4). Inverted $T_2$ distributions in grain-supported carbonates are unimodal, whereas petrography studies show them to be at least bimodal. Petrographs show that the grains are composed of micrite particles, which form the intragranular porosity. The juxtapositioning of pores of diverse sizes, and the diffusion of magnetic moments among these pores, causes the breakdown of the relationship between $T_2$ and pore size. (Assumption 3).

Most recently, we have discovered that NMR tests performed on carbonate rock samples from Middle East oil wells are temperature dependent. The temperature dependencies are contrary to established beliefs for NMR response in fluid-saturated rocks. The prior art was based on the supposition that there were no significant temperature dependencies for the NMR response. Closer examination of this work suggests that these conclusions were valid only for sandstone media. Data obtained for carbonate media were simply inconsistent. Furthermore, a recent comparison of laboratory core data with data obtained from logs taken in the Middle East wells also shows inconsistencies.

The studies made in accordance with the present invention confirm the prior art conclusion with respect to a limited number of sandstone media. That is, the change in response to temperature is weak or non-existent. However, core samples taken from the Middle East wells cited in the comparative data show a dependence on temperature which is consistent with the observed discrepancies between laboratory core data and log data.

The extent of the temperature dependence is very significant for NMR logging interpretation. In particular, the traditional practice of using an empirically determined "cutoff" in the relaxation time distribution becomes completely invalid unless extensive corrections are made to correlations obtained at room temperature.

In the context of more advanced models of NMR in water-saturated rocks, the data is explained only by a temperature dependence of the intrinsic nuclear magnetic relaxivity of the rock pore surfaces. The interpretation methodology recently proposed for dual porosity carbonate systems of the type known as "peloidal grainstones" or "peloidal packstones" still delivers an expected length scale for large, intergranular pores, but fails to deliver a correct length scale for micropores unless it is extended using a laboratory determination of relaxivity as a function of temperature.

Selecting a laboratory correlation appropriate for the known geological and mineralogical characteristics of the sub-surface known a priori from other data, or determined in situ using other logging tools, it is possible to adapt the interpretation of the carbonate rock to account for the temperature dependence. Thus adapted, the methodology delivers length scales for both the intergranular pores and the micropores of the dual porosity systems common in carbonate geology. Although the inferred intergranular pore length scale should be affected only weakly by the temperature effect disclosed herein, the micropore length scale will be affected strongly. Both of these length scales are important in estimating transport properties such as electrical conductivity and hydraulic permeability. The latter is of considerable importance in evaluating subsurface formations, because it determines how easy it is to produce the hydrocarbons which may be present. The former is important, because it affects the interpretation of associated resistivity logs. The resistivity logs are a primary source of data for estimating how much hydrocarbons may be present.

The present invention contemplates two equivalent methods for obtaining reliable NMR results for bound fluid and free fluid in carbonate rock formations based upon adjusting $T_2$ data with respect to temperature. The invention also features a more advanced methodology for ascertaining the rock petrophysical properties, which methodology adapts another application to include the newly discovered temperature dependence of relaxivity.

SUMMARY OF THE INVENTION

The aspect of the invention closest to orthodox practice, features two equivalent methods of achieving reliable results for bound fluid and free fluid. Orthodox practice relies implicitly upon the aforementioned assumptions of: (2) pore independent; (4) additive magnetization decays. The invention retains these assumptions in the first method. The first method allows for an expected variation of surface relaxivity $\rho$ as found experimentally in carbonate rocks, within the application of Eq. 1 of Assumption (3). The methods employ the conventional $T_2$ distribution, which is generally regarded as equivalent to a pore-size distribution, where each pore size "a" (strictly, volume to surface ratio V/S) is associated with a particular relaxation time $T_2$, the proportionality being the surface relaxivity, as in the equation now found in hundreds of sources dealing with NMR logging:

$$1/T_2 = \rho\ S/V = \rho/a \qquad (2)$$

Orthodox practice is to determine by laboratory experiments a so-called "$T_2$ cut-off" or $T_{2c}$, which partitions the distribution into small pores (considered to retain fluid in flows, hence the term "bound fluid") and larger pores (which allow fluid to flow, called "free fluid"). This appears to have a certain validity in experiments conducted at laboratory or room temperatures.

If, however, $\rho$ must be considered to vary with temperature, then NMR logging of downhole formations at temperature $\Theta$ results in the first instance in a $T_2$ distribution appropriate to temperature $\Theta$, which can be called $g^{(\Theta)}(T_2)$. In the orthodox interpretation paradigm, each relaxation time $T_2$ corresponding to a pore size "a" is given by:

$$a = \rho(\Theta)T_2 \qquad (3)$$

But the $T_2$ cut-off, $T_{2c}$, is determined at room temperature RT. This corresponds to a critical pore size, $a_c$:

$$a_c = \rho(RT)T_{2c} \qquad (4)$$

which determines the partition between bound and free fluid.

To make the traditional interpretation of $T_2$ distributions, an analyst must now either (i) adjust $T_2$ distribution $g^{(\Theta)}(T_2)$ to room temperature before applying $T_{2c}$, or (ii) adjust $T_{2c}$ to borehole temperature $\Theta$ before applying the conventional integration to yield bound and free fluid volumes. The procedures are equivalent, but the analysis proceeds by slightly different routes.

In the second, more advanced method of the invention, the so-called "model-based interpretations", which are the subject of the application, Ser. No. 08/932,141, filed Sep. 16, 1997 (incorporated herein by reference) are subject to temperature modifications. These "model-based interpretations" relate to the physics of diffusion in typical carbonate pore geometries. This second method avoids, in particular, the aforementioned pore space Assumption (2), viz. that the pores act independently. This is now believed to be incorrect for carbonates. The second method of the invention includes the temperature dependence of the surface relaxivity, a numerical parameter appearing explicitly in the computational models of the prior application.

The first and second methods will be explained in more detail with reference to the subsequent detailed description in the preferred embodiments.

The temperature at any particular depth in the borehole can be measured by a thermometer in the NMR tool, or it may be known from previous temperature measurements in the borehole or other boreholes in the same field. The temperature can also be derived from empirical relationships relating temperature to depth in the oil or gas field in which the NMR logging is taking place.

It is an object of this invention to provide a new method of determining the bound fluid and free fluid in carbonate rocks.

It is another object of the invention to provide an improved method of using temperature adjusted NMR data to determine the characteristics of carbonate rocks in model-based interpretations, which further improves the estimates of petrophysical parameters by explicit modelling of diffusion within the pore geometry of the rock.

BRIEF DESCRIPTION OF THE DRAWINGS

A complete understanding of the present invention may be obtained by reference to the accompanying drawings, when considered in conjunction with the subsequent detailed description, in which.

DESCRIPTION OF THE PREFERRED EMBODIMENT

Generally speaking, the invention reflects the discovery that carbonate formations yield unreliable, down hole NMR results. These results must be corrected for temperature. The invention features two equivalent methods for obtaining reliable NMR results for bound fluid and free fluid in carbonate rock formations based upon adjusting the $T_2$ data with respect to temperature.

Figure 1:
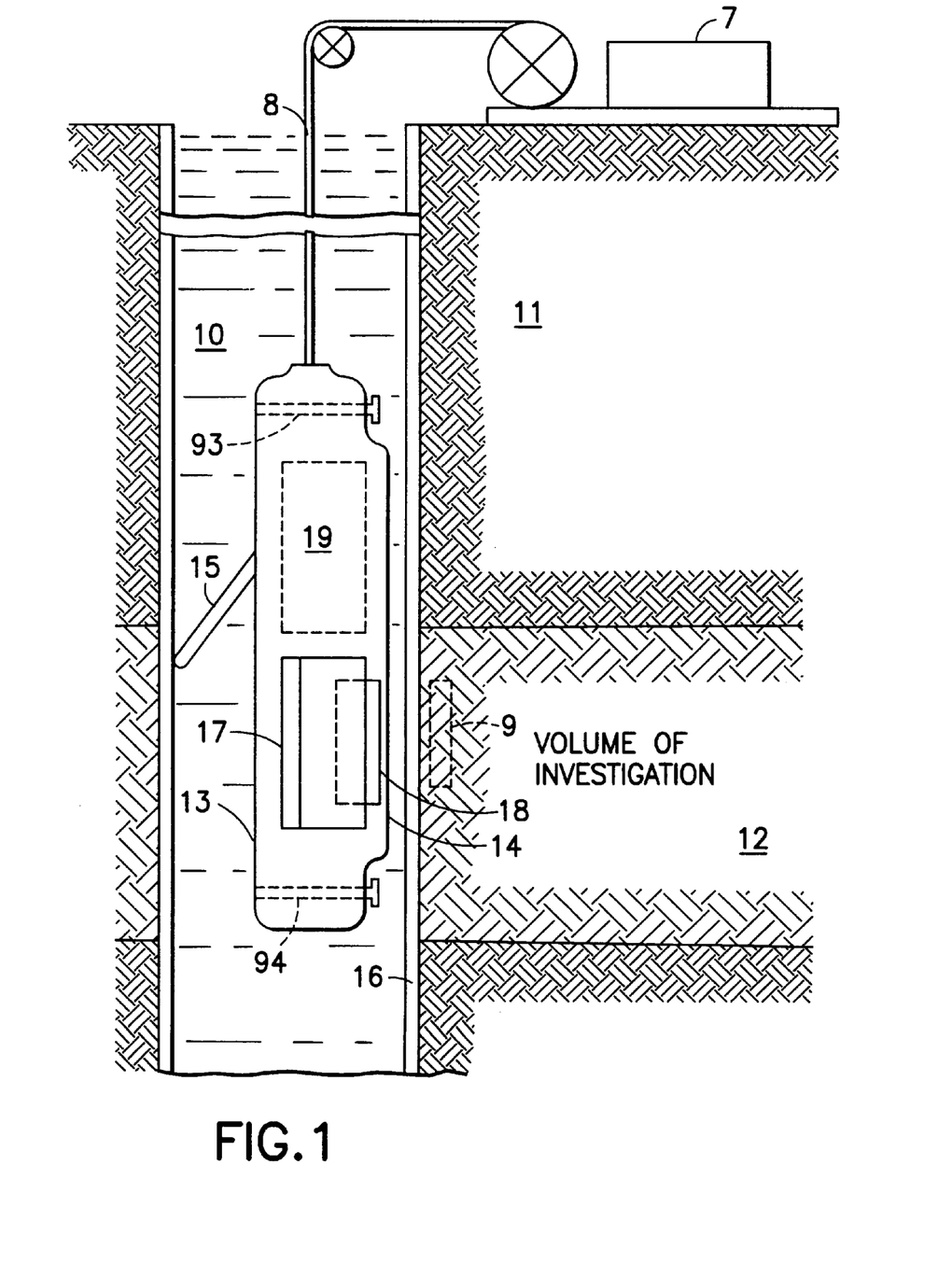
FIG. 1 illustrates a schematic, in situ, side view of a typical down hole NMR instrument positioned in a bore hole for making measurements of the surrounding formations, in accordance with this invention.

Now referring to FIG. 1, a typical NMR tool 13 is shown. The NMR tool 13 is disposed within a borehole 10, adjacent formations 11 and 12. The NMR tool 13 is lowered into the borehole 10 by a wireline 8, which communicates with surface instrumentation 7. The face 14 of the tool is designed to intimately contact the borehole surfaces. A retractable arm 15 is used for this purpose, and presses the NMR tool 13 against the wall of the borehole. The tool comprises a magnetic array 17 and an antenna 18, which are used to create and measure the oscillating magnetic field characteristics associated with NMR testing. Certain aspects of NMR testing also require that the area of investigation be prepolarized, which is accomplished by component 19. A more detailed discussion of this tool and others used for bore hole NMR exploration, can be obtained by reference to U.S. Pat. No. 5,055,787. The NMR tool illustrated in FIG. 1 is excentered in the bore hole, and has a sensing pad that is pushed against the formation, as shown. Other NMR tools can be centralized in the bore hole, such as the tool described in U.S. Pat. No. 4,710,713.

Figure 2:
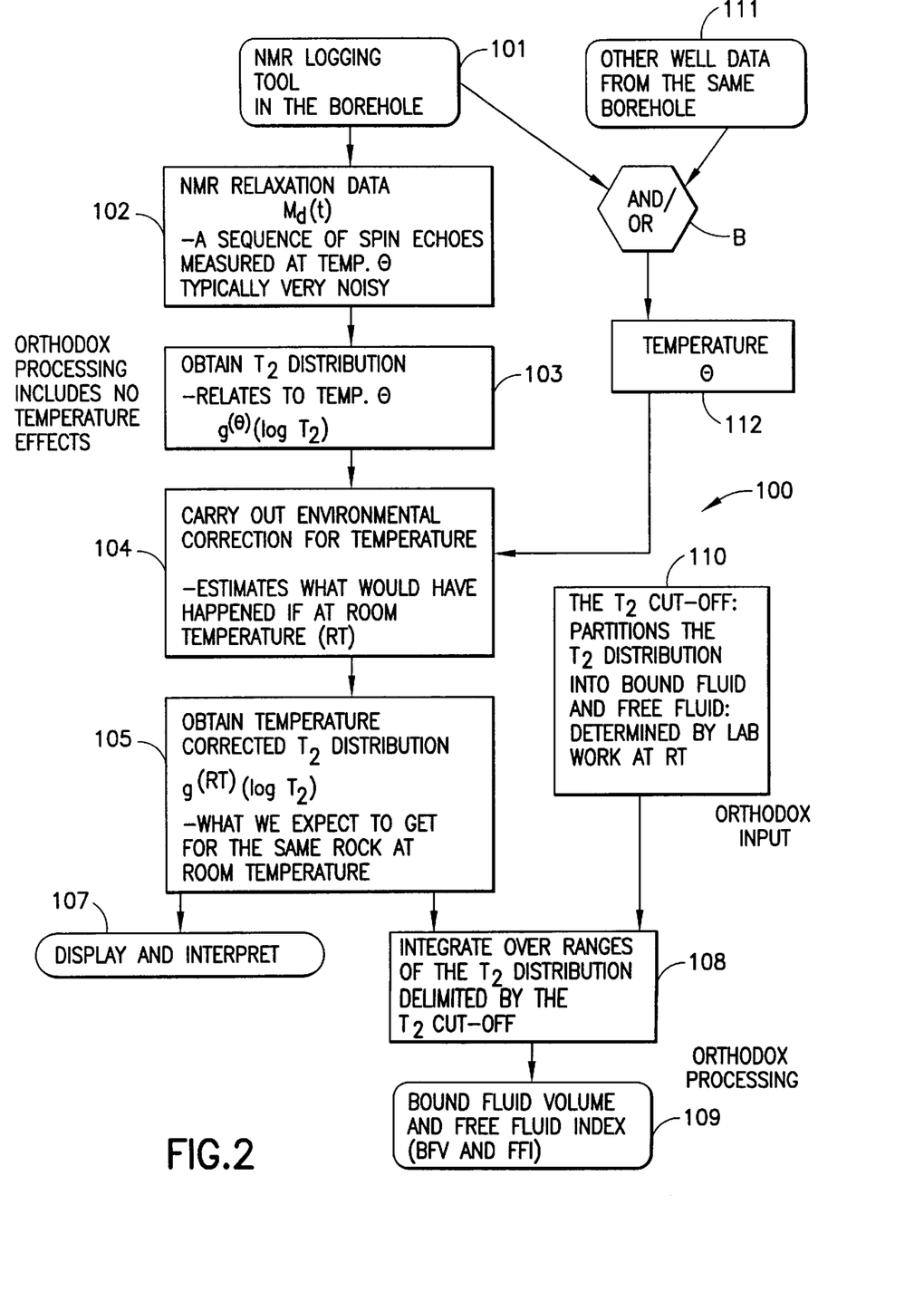
FIG. 2 shows a flow diagram of the temperature adjusted NMR logging procedure of this invention.
Figure 3:
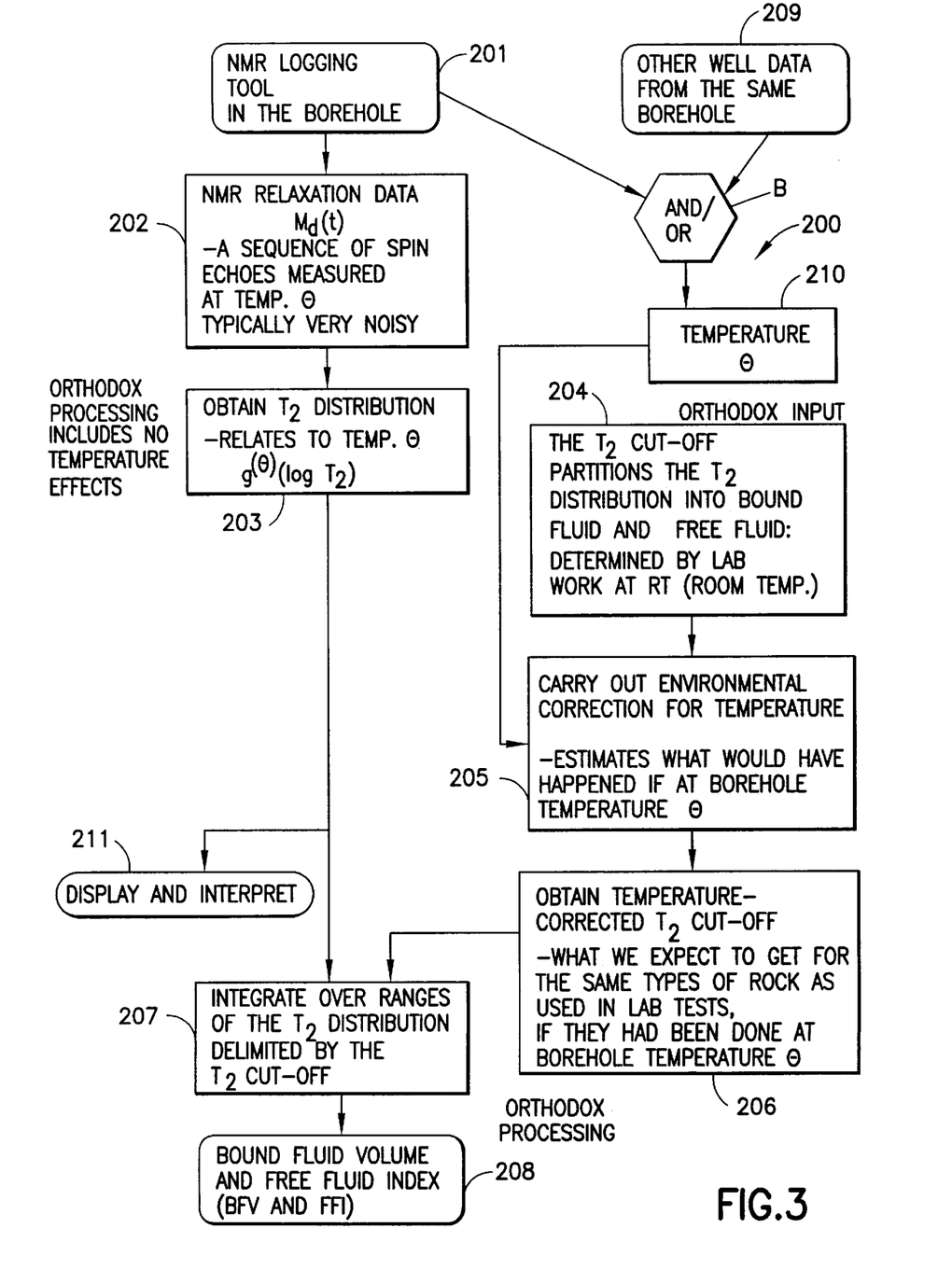
FIG. 3 illustrates a flow diagram of an alternate embodiment of the temperature adjusted NMR logging procedure of this invention.

FIGS. 2 and 3 illustrate, by means of respective flow diagrams 100 and 200, the new temperature adjusted methods of the invention. The methods utilize the common $T_2$ distribution, which is generally regarded as equivalent to a pore-size distribution, in which each pore size "a" (strictly, volume to surface ratio V/S), is associated with a particular relaxation time $T_2$, the proportionality being the surface relaxivity, as in the equation now found in hundred of sources dealing with NMR logging:

$$1/T_2 = \rho\ S/V = \rho/a \tag{5}$$

Conventional practice is to determine by laboratory experiments a so-called "$T_2$ cut-off" or $T_{2c}$, which partitions the distribution into small pores, considered to retain fluid in flows (hence "bound fluid") and larger pores, which allow fluid to flow (hence "free fluid").

If, however, $\rho$ is considered to vary with temperature, then NMR logging of down hole formations at temperature $\Theta$ results in the first instance in a new $T_2$ distribution appropriate to temperature $\Theta$, which can be called $g^{(\Theta)}(T_2)$. In the orthodox interpretation paradigm, each relaxation time $T_2$ corresponding to a pore size "a" is given by:

$$a = \rho(\Theta)T_2 \tag{6}$$

But the $T_2$ cut-off, $T_{2c}$ is determined at room temperature RT. This corresponds to a critical pore size, $a_c$:

$$a_c = \rho(RT)T_{2c} \tag{7}$$

which determines the partition between bound and free fluid.

To make the traditional interpretation of $T_2$ distributions, the analyst now either (i) adjusts $T_2$ distribution $g^{(\Theta)}(T_2)$ to room temperature before applying $T_{2c}$, or (ii) adjusts $T_{2c}$ to borehole temperature $\Theta$ before applying the conventional integration to yield bound and free fluid volumes.

To make the traditional interpretation of $T_2$ distributions, the new method of the invention can either (i) adjust the $T_2$ distribution $g^{(\Theta)}(T_2)$ to room temperature before applying $T_{2c}$, or (ii) adjust $T_{2c}$ to borehole temperature $\Theta$ before applying the conventional integration to yield bound and free fluid volumes. These equivalent procedures are illustrated in FIGS. 2 and 3, respectively, described in greater detail hereinbelow. The only difference is whether the analyst chooses to present the general display of $T_2$ data referenced to borehole temperature $\Theta$ as shown in FIG. 3, or to room temperature, as illustrated in the method shown in FIG. 2.

The method of FIG. 2 (room temperature referencing) is consistent with the generic practice of performing "environmental corrections" to well log data, obtained by an appropriate tool shown in FIG. 1. The data is presented in terms of what would be expected, as if the measurement had been performed at room temperature, rather than at temperature $\Theta$.

It is commonly assumed that $\rho$ is uniform throughout the rock pores. Making this simple assumption, and assuming that the quantity of fluid in pores of size "a" does not change with temperature, the pore size can be related to $T_2$ at the two temperatures by:

$$a = \rho(RT)T_2(a, RT) = \rho(\Theta)T_2(a, \Theta) \tag{8}$$

On a logarithmic scale of $T_2$ (as conventionally used) this amounts to a shift in the curve for $g^{(\Theta)}$ to obtain $g^{(RT)}$, by a fixed distance $\log(\rho(\Theta)/\rho(RT))$, where the ratio $\rho(\Theta)/\rho(RT)$ can be determined in the laboratory. This is the method shown in FIG. 2.

Figure 4:
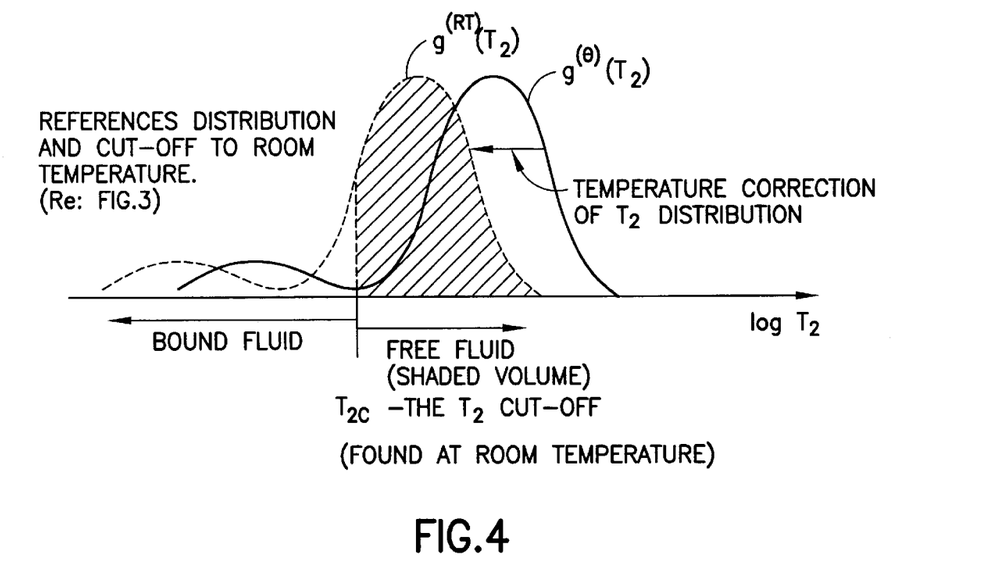
FIG. 4 shows a graph depicting how the $T_2$ distribution is adjusted for temperature utilizing the procedure shown in FIG. 2.

FIG. 4 depicts a graph of free fluid vs. $g(T_2)$ It can be seen that referencing the data to room temperature results in shifting the curve leftwardly from $g^{(\Theta)}(T_2)$ to $g^{(RT)}(T_2)$ as a function of temperature correction.

Alternatively, the method of FIG. 3 can be used to adjust $T_{2c}$ for temperature, instead, because the critical pore size $a_c$ dividing free from bound fluid stays the same. Because of the difference in $\rho$, consider:

$$a_c = \rho(RT)T_{2c}(RT) = \rho(\Theta)T_{2c}(\Theta) \tag{9}$$

or equivalently:

$$T_{2c}(\Theta) = T_{2c}(RT)\ [\rho(RT)/\rho(\Theta)] \tag{10}$$

Figure 5:
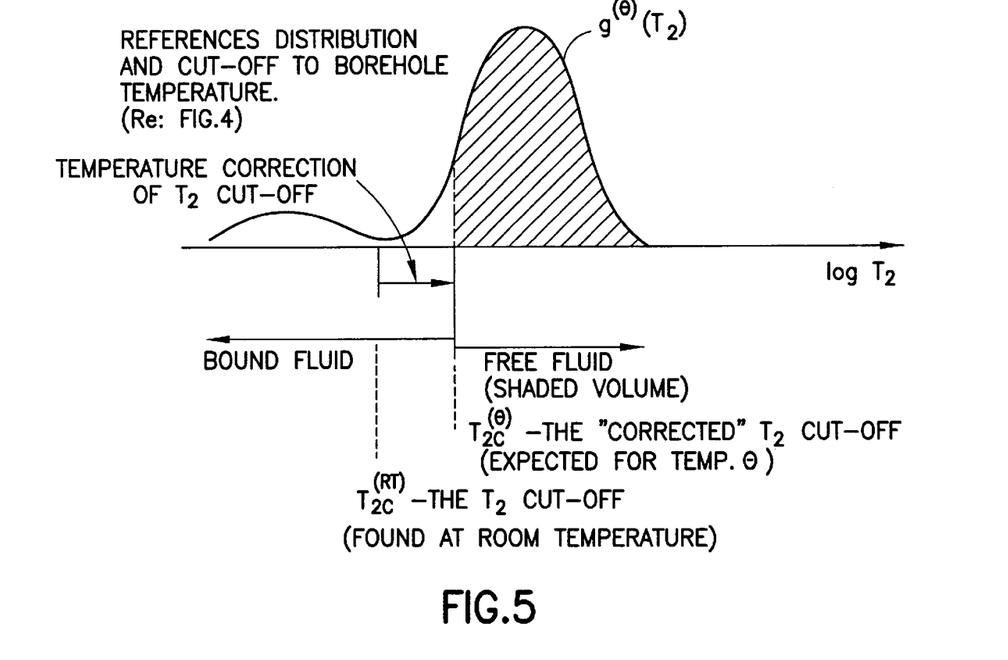
FIG. 5 illustrates a graph depicting how the $T_2$ distribution is adjusted for temperature utilizing the procedure shown in FIG. 3.

Again, on the conventional log $T_2$ axis, this amounts to a shift of the position of $T_{2c}$ by an amount of log $(\rho(RT)/\rho(\Theta))$, as shown in FIG. 5. Note that this is the same distance, but in the opposite sense, to the shift applied to $g^{(\Theta)}$ to obtain $g^{(RT)}$ of FIG. 4 pursuant to the method of FIG. 2.

The methods of FIGS. 2 and 3 are mathematically equivalent. However, the method in FIG. 2 references all of the data to room temperature, which is more consistent with traditional practices of "environmental corrections" in log analysis generally; whereas the method in FIG. 3 references data to borehole temperature. The method of FIG. 3 is slightly easier to explain, by reason of the critical pore size $a_c$, which remains almost unchanged, while its associated relaxation time varies according to any change in relaxivity $\rho$.

Now referring once again to FIG. 2, a flow chart 100 of this invention features correcting the data in the borehole for temperature variation of the relaxivity, $\rho$. The NMR tool 13 (FIG. 1) is placed in the borehole, step 101. The spin echoes of the NMR relaxation data are measured at temperature $\Theta$, step 102. A $T_2$ distribution as it relates to temperature $\Theta$ is then obtained, step 103. In accordance with the invention, the $T_2$ distribution must then be temperature corrected with regard to environmental correction, step 104, to obtain the temperature-corrected $T_2$ distribution, step 105. The results are then displayed and interpreted, step 107. The data is then integrated over the $T_2$ distribution ranges, step 108, delimited by the $T_2$ cut-off, and the bound fluid volume and the free fluid index is determined, step 109. The integration step 108 uses the conventional input of the $T_2$ cut-off 110 to partition the $T_2$ distribution. As with the conventional, prior art method, other well data 111 may be introduced at point B, along with the measurement of temperature $\Theta$, step 112.

Now referring to FIG. 3, depicting an alternate method 200 of this invention, relaxivity $\rho$ is corrected for temperature variation in the laboratory (i.e., at room temperature (RT)). The NMR tool 10 is introduced into the borehole, step 201. The relaxation data at temperature $\Theta$ is measured, step 202. The $T_2$ distribution is obtained as it relates to temperature $\Theta$, with no adjustment for temperature, step 203. The $T_2$ cut-off partitioning the $T_2$ distribution determined in the laboratory at room temperature RT, step 204, is used in accordance with the invention to carry out the environmental correction for temperature at the borehole temperature $\Theta$, step 205. The new temperature-corrected $T_2$ cut-off is obtained, step 206. This data is then used to adjust the $T_2$ distribution for the integration, step 207, thus obtaining the bound fluid volume and the free fluid index, step 208. As with conventional procedures, other well data 209 can be introduced at point B, while measuring the temperature $\Theta$, step 210, which is used to adjust the $T_2$ cut-off, steps 205 and 206. The $T_2$ distribution at temperature $\Theta$ can be displayed, step 211, for further analysis.

Figure 6:
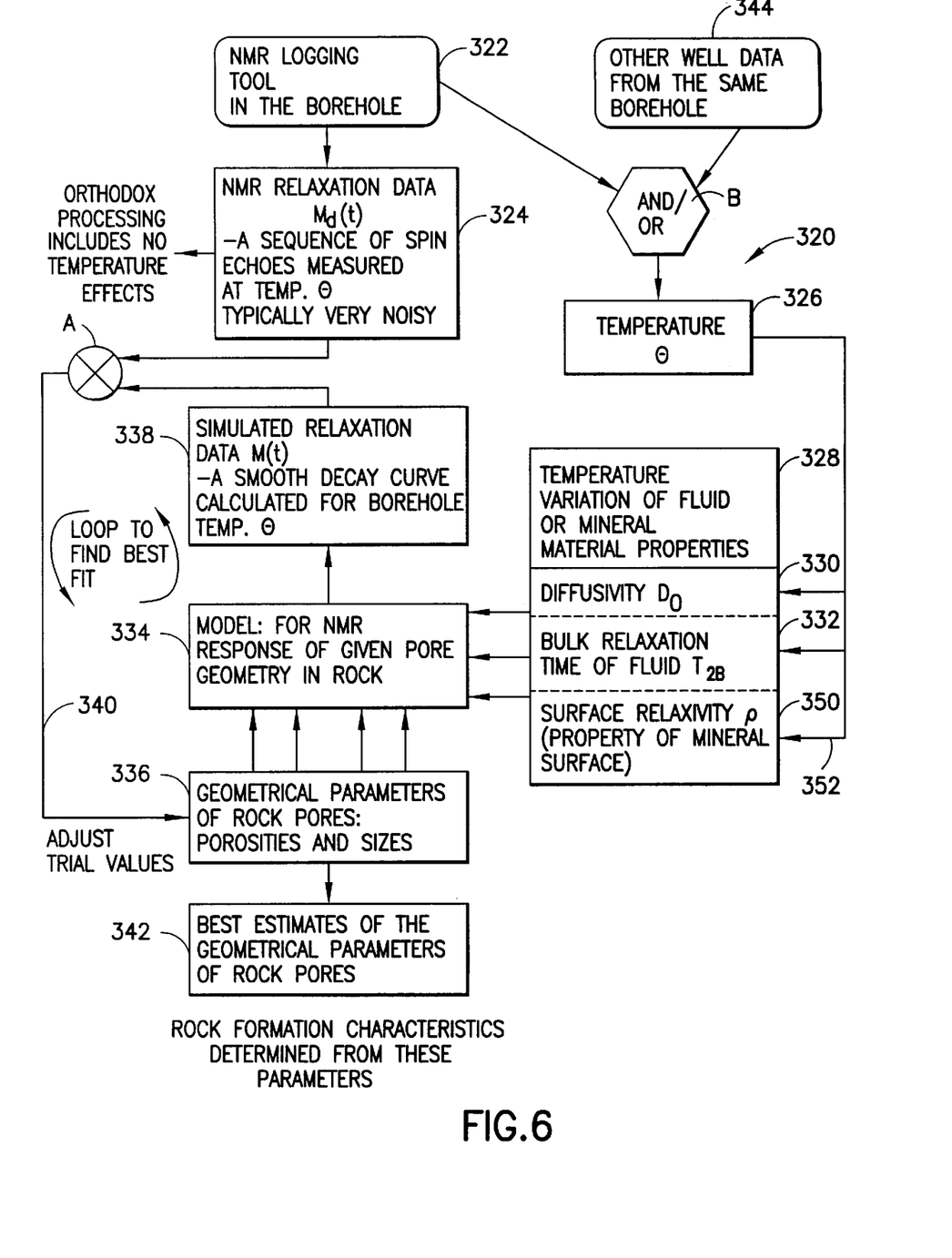
FIG. 6 depicts a flow diagram of a more advanced method of NMR logging which illustrates a temperature modified model of the prior application teachings.
Figure 7:
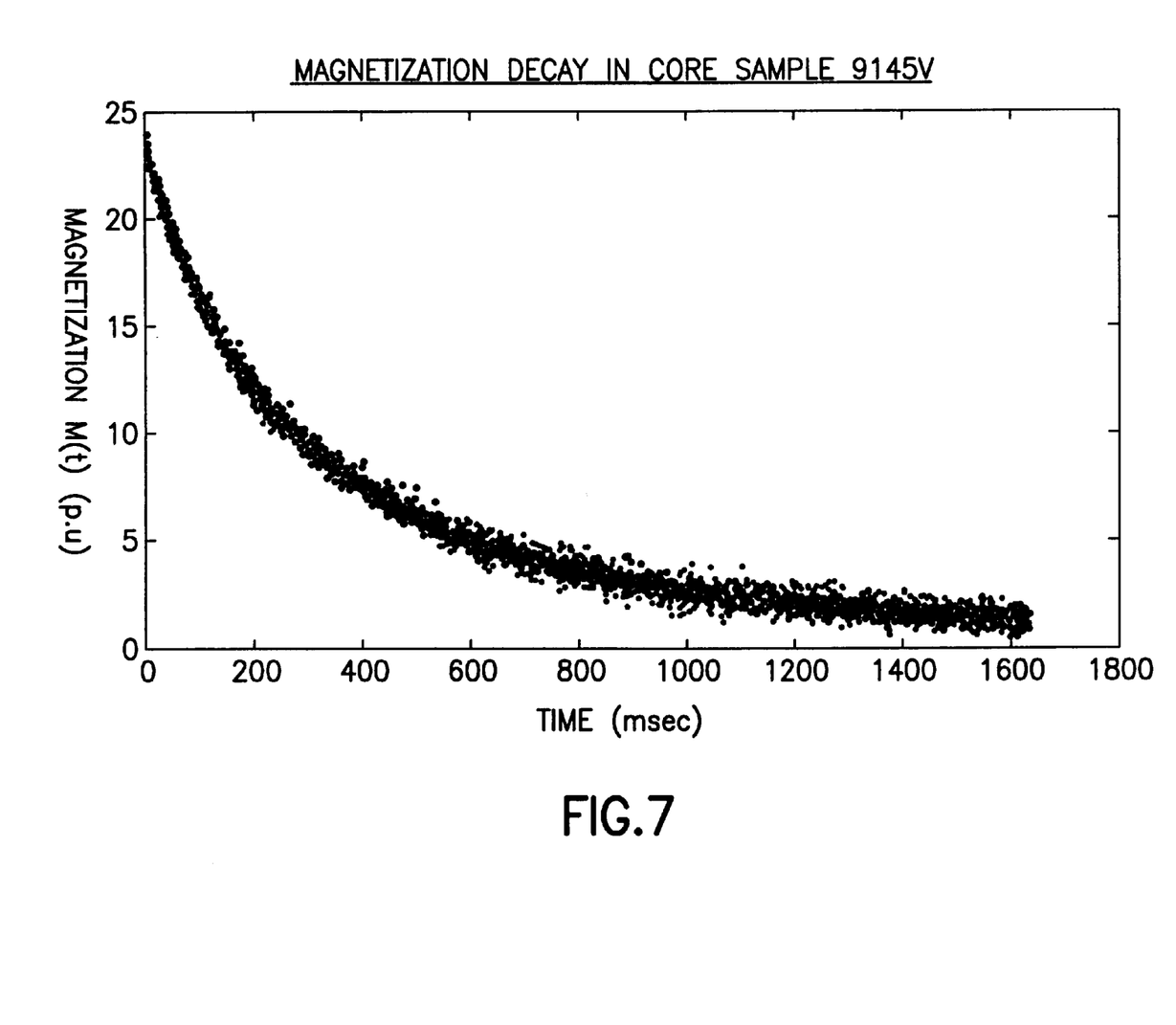
FIG. 7 shows a graph of example relaxation data which might be obtained downhole.

Referring to FIG. 6, a flow diagram 20 illustrates the more advanced procedure, used for NMR logging utilizing the logging tool 13, shown in FIG. 1. The logging tool 13 is lowered into the borehole, step 322. NMR relaxation data is obtained by the tool 13 without adjusting for temperature, step 324. This data is typically very noisy, as shown in FIG. 7. Other well data from the same borehole (block 344) can be combined with the temperature data at point B to obtain accurate data for subsequent method steps (blocks 328, 330 and 332), respectively.

The parameters diffusivity $D_o$ (block 330), bulk relaxation $T_{2B}$ (block 332) and relaxivity $\rho$ (block 350) are determined by laboratory studies, so that they are assumed known a priori in the flow diagram of FIG. 6.

The logging tool 13 measures temperature, block 326, for inclusion into the temperature dependent physical data of the interpretation algorithm, steps 328, 330, and 332. The data includes fluid or mineral material properties, step 328, diffusivity, step 330, and bulk relaxation time, step 332. This data is used to construct a model for the NMR response of a given pore geometry in the rock formation, step 334.

In accordance with the novel aspects of this invention, surface relaxivity, $\rho$, which is a property of the mineral surface, is also used, step 350, to construct the model of block 334. Until this invention, the relaxivity, $\rho$, was never adjusted for temperature shown via line 352.

Figure 8:
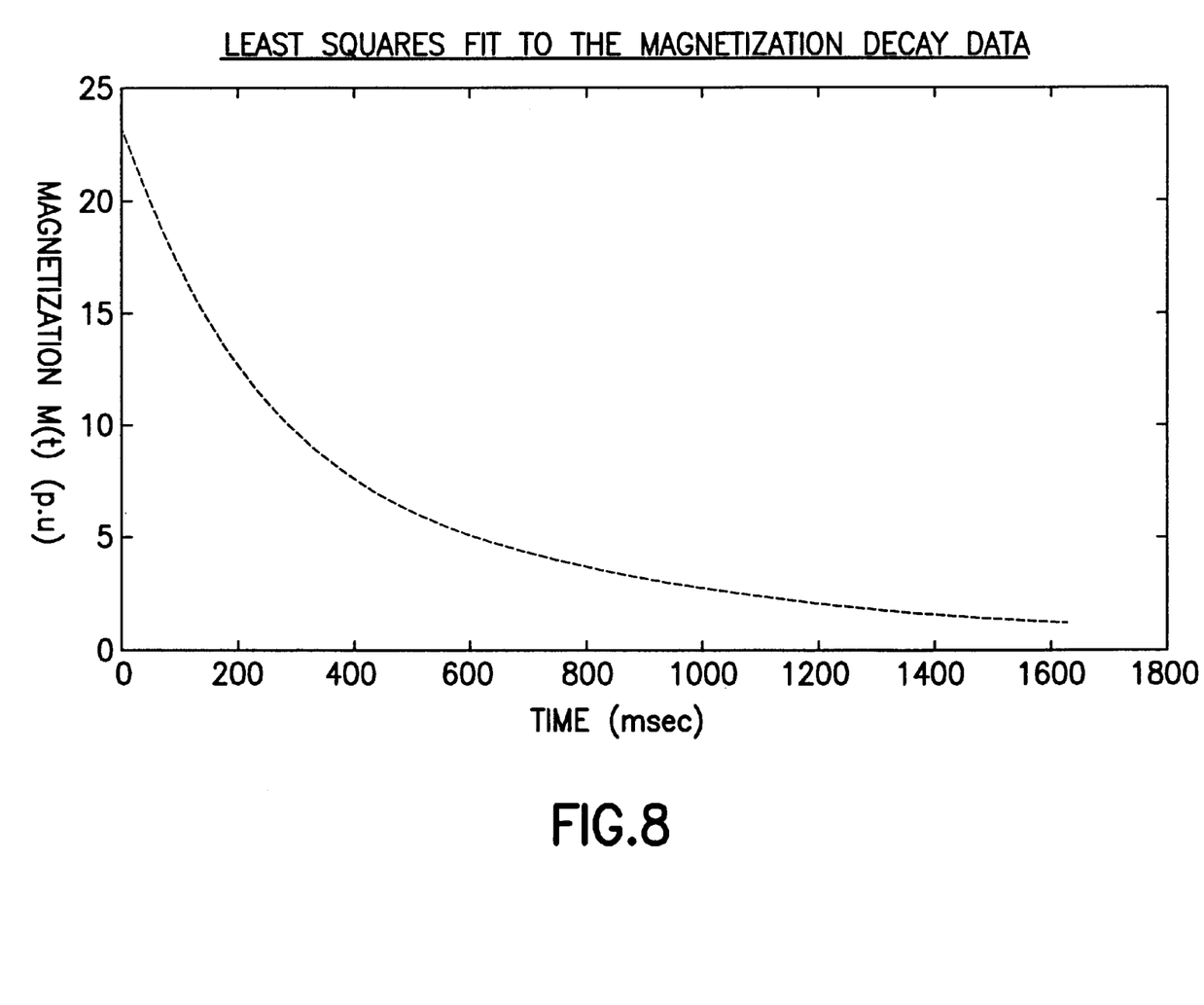
FIG. 8 illustrates a graph depicting a smoothed curve of noise-free relaxation data computed by the model-based inversion procedure expressed in FIG. 6, and based upon the actual data shown in FIG. 7.

Trial values for the geometrical parameters of the rock pores, step 336, are also used to construct the model 334. Next, simulated relaxation data, step 338, is obtained from the NMR model 334, and combined at point A with actual measured NMR relaxation data, step 324. The combined data, line 340, is used to adjust the geometrical parameters, step 336, to obtain the best fit. At that point, the simulated relaxation data of step 338 is a "best, least squares fit", as shown by the smoothed curve in FIG. 8. Best estimates of the geometrical parameters are outputed in step 342. These best estimates are then used to estimate rock petrophysical characteristics such as permeability, or electrical resistivity.

Since other modifications and changes varied to fit particular operating requirements and environments will be apparent to those skilled in the art, the invention is not considered limited to the example chosen for purposes of disclosure, and covers all changes and modifications which do not constitute departures from the true spirit and scope of this invention.

Having thus described the invention, what is desired to be protected by letters patent is presented in the subsequently appended claims.

What is claimed is:

1. A NMR logging system for obtaining accurate formation characteristics in a bore hole, comprising:

a formation probing instrument having means for measuring NMR relaxation in formations down hole, said instrument having additional temperature measuring means for measuring the temperature;

recording means operatively connected to said formation probing instrument for recording data of down hole measurements of relaxation, and temperature; and processing means associated with said recording means for adjusting said relaxation measurements with respect to a temperature difference between downhole temperature and room temperature in order to obtain accurate formation characteristics.

2. The NMR logging system in accordance with claim 1, wherein said formation probing instrument comprises a tool with a sensor pad that is pressed against the formation.

3. The NMR logging system in accordance with claim 1, wherein said formation probing instrument comprises an NMR tool adapted to be centered in the bore hole.

4. A logging method for obtaining accurate formation characteristics in a bore hole, comprising the steps of:

(a) obtaining NMR relaxation data down hole;

(b) adjusting said obtained NMR relaxation data with respect to a temperature difference between room temperature and downhole temperature; and (c) utilizing said adjusted NMR relaxation data in establishing formation characteristics.

5. The logging method in accordance with claim 3, wherein said formation comprises carbonate rock.

6. A NMR logging system for obtaining accurate formation characteristics in a bore hole, comprising:

a formation probing instrument having means for measuring NMR relaxation in formations down hole, said instrument having additional temperature measuring means for measuring the temperature;

processing means associated with said probing instrument for adjusting said relaxation measurements to downhole temperature; and recording means operatively connected to said formation probing instrument for recording the adjusted data for providing accurate formation characteristics.

7. The NMR logging system in accordance with claim 6, wherein said formation probing instrument comprises a tool with a sensor pad that is pressed against the formation.

8. A logging method for obtaining accurate formation characteristics in a bole hole, comprising the steps of:

(a) obtaining NMR relaxation data down hole;

(b) adjusting said NMR relaxation data for downhole temperature; and (c) utilizing said NMR relaxation data of step (b) in establishing formation characteristics.

9. The logging method in accordance with claim 8, wherein said formation comprises carbonate rock.

10. A method for obtaining accurate formation characteristics in a bore hole, comprising the steps of:

a) obtaining NMR relaxation data down hole and obtaining a $T_2$ distribution $g^{(\Theta)}$ (log $T_2$) therefrom;

b) environmentally correcting said $T_2$ distribution data to obtain a $T_2$ distribution $g^{(RT)}$ (log $T_2$), that is room temperature referenced;

c) determining bound fluid volume and free fluid index, dependent upon said relaxation data and said room temperature referenced $T_2$ distribution; and d) establishing formation characteristics dependent upon said NMR relaxation data and said temperature referenced $T_2$ distribution.

11. The method in accordance with claim 10, the steps further comprising:

e) partitioning said $T_2$ distribution into bound fluid and free fluid; and f) integrating said corrected $T_2$ distribution prior to determining bound fluid volume and free fluid index.

12. The method in accordance with claim 11, wherein said formation comprises carbonate rock.

13. A method for obtaining accurate formation characteristics in a bore hole, comprising the steps of:

a) obtaining NMR relaxation data down hole;

b) obtaining a $T_2$ distribution $g^{(\Theta)}$ (log $T_2$) from said NMR relaxation data;

c) obtaining a $T_2$ cut-off referenced to borehole temperature;

d) integrating said $T_2$ distribution over ranges delimited by said temperature referenced $T_2$ cut-off; and e) establishing formation characteristics dependent upon said adjusted NMR relaxation data.

14. The method in accordance with claim 13, the steps further comprising:

f) determining bound fluid volume and free fluid index, dependent upon said relaxation data and said $T_2$ distribution.

15. The method in accordance with claim 13, wherein said formation comprises carbonate rock.

16. A method for obtaining accurate formation characteristics in a bore hole, comprising the steps of:

(a) obtaining relaxation data downhole;

(b) constructing a NMR model for a given pore geometry of a rock formation using geometrical parameters of the rock pores, and, inter alia, temperature dependent surface relaxivity;

(c) obtaining simulated relaxation data obtained from the NMR model constructed in step (b);

(d) combining the NMR relaxation data of step (a) with simulated relaxation data of step (c);

(e) adjusting the geometrical parameters of the rock pores to obtain a best fit; and (f) estimating the rock formation characteristics based upon the adjusted geometrical parameters of step (e).

17. The method in accordance with claim 16, wherein the model construction step (b) includes the further step of:

(g) estimating temperature downhole.

18. The method in accordance with claim 16, wherein the model construction step (b) includes the further step of:

(g) measuring temperature downhole.

19. The method in accordance with claim 16, wherein the NMR model constructing step (b) includes the further step of:

(h) using diffusivity $D_o$ estimated a priori.

20. The method in accordance with claim 16, wherein the NMR model constructing step (b) includes the further step of:

(h) using bulk relaxation $T_{2B}$ estimated a priori.

21. The method in accordance with claim 16, wherein the NMR model constructing step (b) includes the further step of:

(h) using surface relaxivity $\rho$ estimated a priori.

22. The method in accordance with claim 16, wherein the model constructing step (b) includes the further steps of:

(h) deriving downhole temperature;

(i) estimating diffusivity $D_o$ a priori;

(j) estimating bulk relaxation $T_{2B}$ a priori; and (k) estimating surface relaxivity $\rho$ a priori.

* * * * *